US012588942B2

(12) United States Patent　　(10) Patent No.:　US 12,588,942 B2
Williams et al.　　(45) Date of Patent:　　Mar. 31, 2026

(54) CONTINUOUS ROTATION OF A SURGICAL INSTRUMENT

(71) Applicant: Conmed Corporation, Largo, FL (US)

(72) Inventors: Mason Williams, Centennial, CO (US); Julia Concelman, Cranberry Township, PA (US)

(73) Assignee: Conmed Corporation, Largo, FL (US)

( * ) Notice: Subject to any disclaimer, the term of this patent is extended or adjusted under 35 U.S.C. 154(b) by 1112 days.

(21) Appl. No.: 17/288,022

(22) PCT Filed: Oct. 24, 2019

(86) PCT No.: PCT/US2019/057788
§ 371 (c)(1),
(2) Date: Apr. 23, 2021

(87) PCT Pub. No.: WO2020/086801
PCT Pub. Date: Apr. 30, 2020

(65) Prior Publication Data
US 2021/0393318 A1　　Dec. 23, 2021

Related U.S. Application Data

(60) Provisional application No. 62/749,841, filed on Oct. 24, 2018.

(51) Int. Cl.
*A61B 18/14*　　(2006.01)
*A61B 18/00*　　(2006.01)

(52) U.S. Cl.
CPC ...... *A61B 18/1445* (2013.01); *A61B 18/1482* (2013.01); *A61B 2018/00178* (2013.01);
(Continued)

(58) Field of Classification Search
None
See application file for complete search history.

(56) References Cited

U.S. PATENT DOCUMENTS

| | | |
|---|---|---|
| 9,351,754 B2 | 5/2016 | Vakharia et al. |
| 10,376,302 B2 | 8/2019 | Prisco et al. |

(Continued)

FOREIGN PATENT DOCUMENTS

| | | |
|---|---|---|
| JP | 2005520593 A | 7/2005 |
| JP | 2012070857 | 4/2012 |
| JP | 2017513560 | 6/2017 |

OTHER PUBLICATIONS

International Search Report Form PCT/ISA/220, International Application No. PCT/US2019/057788, pp. 1-8, Dated Dec. 13, 2019.

(Continued)

*Primary Examiner* — Sean W Collins
*Assistant Examiner* — Nora W Rhodes
(74) *Attorney, Agent, or Firm* — Bond, Schoeneck & King, PLLC; David L. Nocilly

(57) ABSTRACT

A continuous rotation assembly that may be positioned in the housing of an electrosurgical device to maintain electrical continuity between an electrosurgical power source and an electrosurgical implement positioned at the end of a rotatable shaft. A stator is positioned about the shaft and fixed against rotation and includes a pair of rings that are electrically isolated from each other. A rotor having first and second sets of pins that are electrically isolated from each other is positioned about the shaft and rotatable therewith. The pins are positioned to stay contact with the pair of rings as the shaft and rotor rotate. A first pair of wires couples the pins to the electrosurgical implement. A second pair of wires couples the pair of rings to an electrosurgical power source, thereby providing power to the implement even if the shaft is rotated continuously.

5 Claims, 3 Drawing Sheets

(52) U.S. Cl.
CPC .............. *A61B 2018/00202* (2013.01); *A61B 2018/00589* (2013.01); *A61B 2018/00601* (2013.01)

(56) References Cited

U.S. PATENT DOCUMENTS

| 10,959,769 B2 | 3/2021 | Mumaw et al. |
| 2015/0025571 A1 | 1/2015 | Suzuki et al. |
| 2015/0272569 A1* | 10/2015 | Leimbach ................. B25F 5/00 |
| | | 227/175.1 |
| 2016/0270842 A1* | 9/2016 | Strobl ................ A61B 18/1445 |
| 2018/0206884 A1 | 7/2018 | Beaupre |
| 2019/0000470 A1* | 1/2019 | Yates .................... H01R 39/34 |
| 2019/0049752 A1* | 2/2019 | Van Heugten ......... G02C 7/083 |

OTHER PUBLICATIONS

CN Office Action, App. No. 2021521955, dated Apr. 14, 2022, pp. 1-11.
Notice of Preliminary Rejection, issued by the Korean Intellectual Property Office (KIPO), Application No. 10-2021-7012330, dated Jan. 18, 2023, pp. 3-9.
CN Office Action, Application No. 201980069877.7, dated Sep. 27, 2023, entire document.

\* cited by examiner

CONTINUOUS ROTATION OF A SURGICAL INSTRUMENT

CROSS-REFERENCES TO RELATED APPLICATIONS

This application is a national stage application under 35 U.S.C. 371 based on international patent application PCT/US19/57788 filed on Oct. 24, 2019, which claims priority to U.S. Provisional Patent Application Ser. No. 62/749,841 filed on Oct. 24, 2018, the entireties of which are incorporated herein by reference.

BACKGROUND OF THE INVENTION

1. Field of the Invention

The present invention relates to surgical instruments and, more specifically, to an approach for allowing a surgical instrument to having electrically powered components that can be continuously rotated though 360 degrees.

2. Description of the Related Art

Surgical instruments, such as electrosurgical vessel sealers and scalpels, have jaws or other implements positioned at the end of an elongated shaft so that the implements can be easily applied to tissue to be treated. The implements may be electrically powered, such as through the use of radiofrequency energy supplied by an electrical generator that is electrically coupled to the implements. The conventional approach for coupling the implements to the generator is to use current carrying wires. However, many types of surgical devices are designed so that the implements can be rotated. While wired devices may be rotated a certain amount, at some point, further rotation will be limited by the length of the wires that extend between non-rotational elements and the rotating elements. In extreme cases, additional rotation of the implements can cause a disconnection of the wires and loss of electrical function. Thus, there is a need in the art for an approach that can deliver electrical continuity to the powered implements of a surgical device while allowing the user to rotate the implements as much as he or she deems necessary without any concern of loss of power or damage to the device.

BRIEF SUMMARY OF THE INVENTION

The present invention comprises a continuous rotation assembly that may be positioned in the housing of an electrosurgical device to maintain electrical continuity between an electrosurgical power source and an electrosurgical implement positioned at the end of a rotatable shaft. The present invention comprises a stator having a pair of rings that are electrically isolated from each other. The stator is positioned about the shaft and fixed against rotation. A rotor having first and second sets of pins that are electrically isolated from each other is positioned about the shaft and rotatable therewith. The rotor includes a first set of pins positioned in contact with one of the pair of rings and a second set of pins positioned in contact with the other of the pair of rings. A pair of wires may be coupled to the pair of rings, respectively, to allow for interconnection to an electrosurgical power source. A housing of the device may define a first rib positioned in abutting relation to the stator to prevent rotation of the stator. The housing may further define a second rib positioned adjacently to the rotor. A bushing may be positioned between the rotor and the second rib to allow for easier rotation of the rotor. The shaft may include a longitudinal slot that engages a tang of the rotor so that they rotate together. The first and second sets of pins may be pogo pins to ensure engagement with the rings. The electrosurgical implement may have first and second opposing jaws, wherein each of the first and second opposing jaws is electrically coupled to a respective one of the first and second sets of pins by each of a second pair of wires.

The present invention also comprises a method of providing continuous rotation to an electrosurgical device. One step involves coupling a rotor having first and second sets of pins electrically isolated from each other to a rotatable shaft of the electrosurgical device so that the first set of pins are positioned in contact with one of a pair of rings of a stator that is fixed against rotation and the second set of pins are positioned in contact with the other of the pair of rings. Another step involves coupling the first and second sets of pins to an electrosurgical implement of the electrosurgical device that is mounted to the shaft. A further step involves coupling the pair of rings of the stator to an electrosurgical power source so that the electrosurgical power source is in electrical continuity with the electrosurgical implement. The method may additionally include the step of rotating the shaft to cause rotation of the rotor while the stator remains fixed so that electrical continuity is maintained between the electrosurgical power source and the electrosurgical implement as a result of the first and second sets of pins remaining in contact with the pair of rings as the shaft is rotated.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
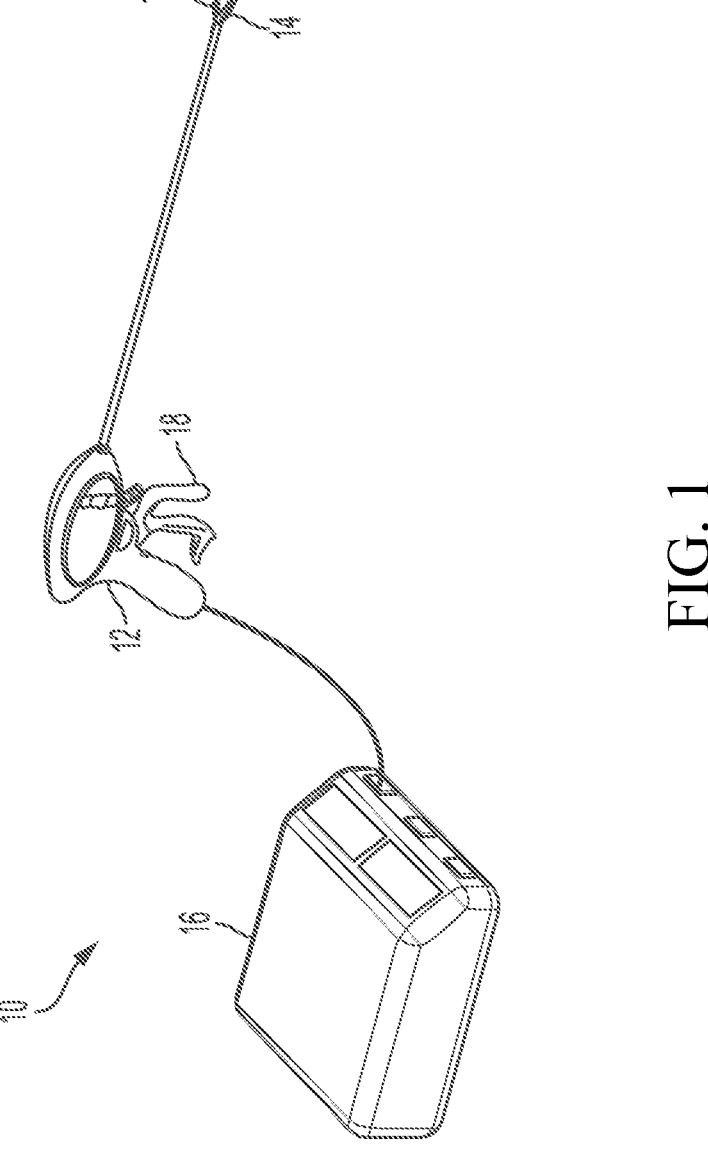
FIG. 1 is perspective view of a surgical device having electrical continuity and continuous rotation according to the present invention.

Referring to the figures, wherein like numeral refer to like parts throughout, there is seen in FIG. 1 a surgical device 10 having a continuous rotation assembly 12 for providing electrical continuity to a surgical instrument, illustrated as a pair of electrosurgical jaws 14 at the end of a shaft 18, that are coupled to a electrosurgical power source 16, such as an electrosurgical generator. It should be recognized that the present invention could be incorporated into other surgical devices having an implement that is coupled to source of electrosurgical power source 16, such as electrosurgical forceps, electrosurgical pencils, and the like.

Figure 2:
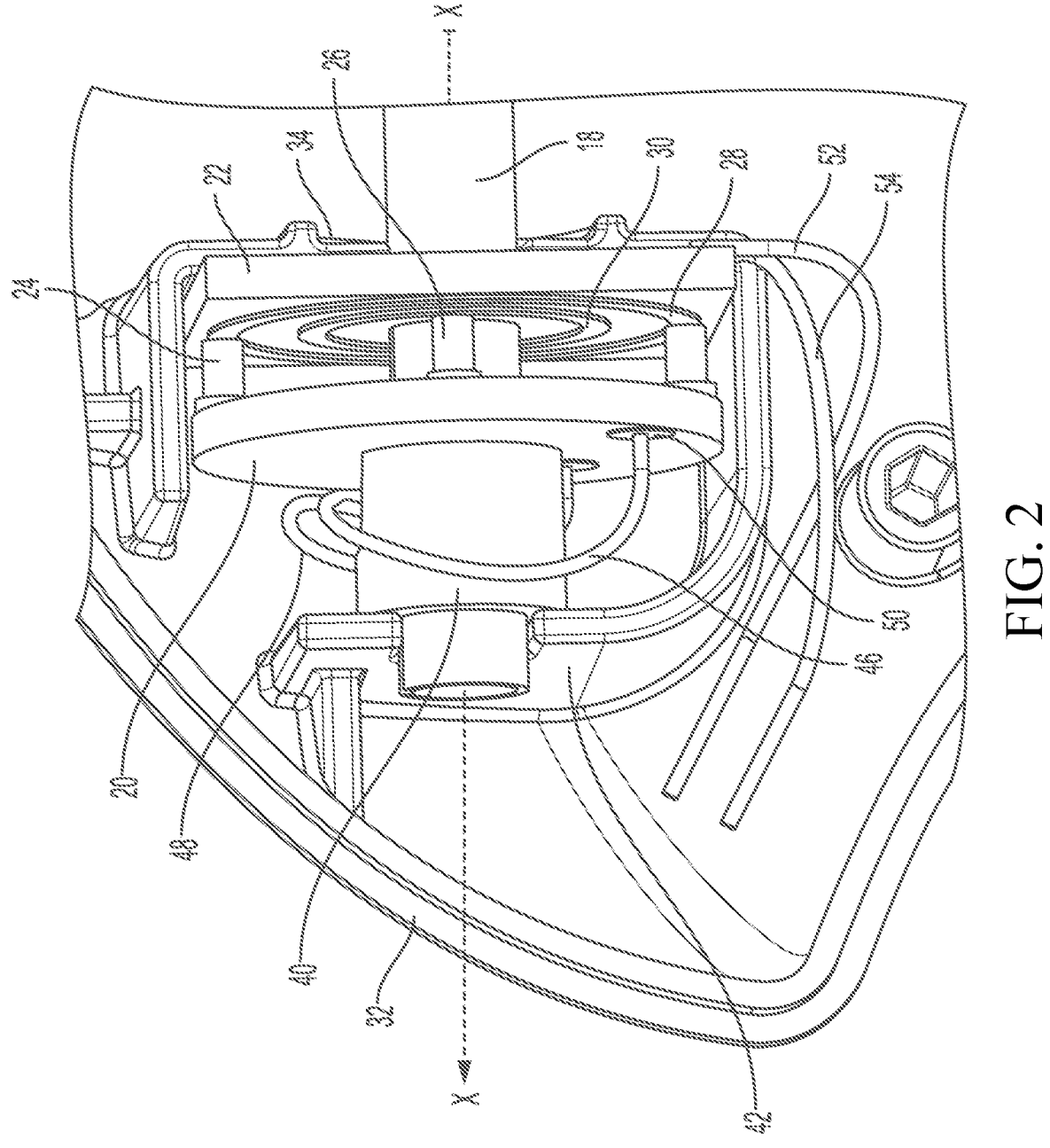
FIG. 2 is an isometric view of an assembly for providing electrical continuity and continuous rotation in a surgical device according to the present invention.
Figure 3:
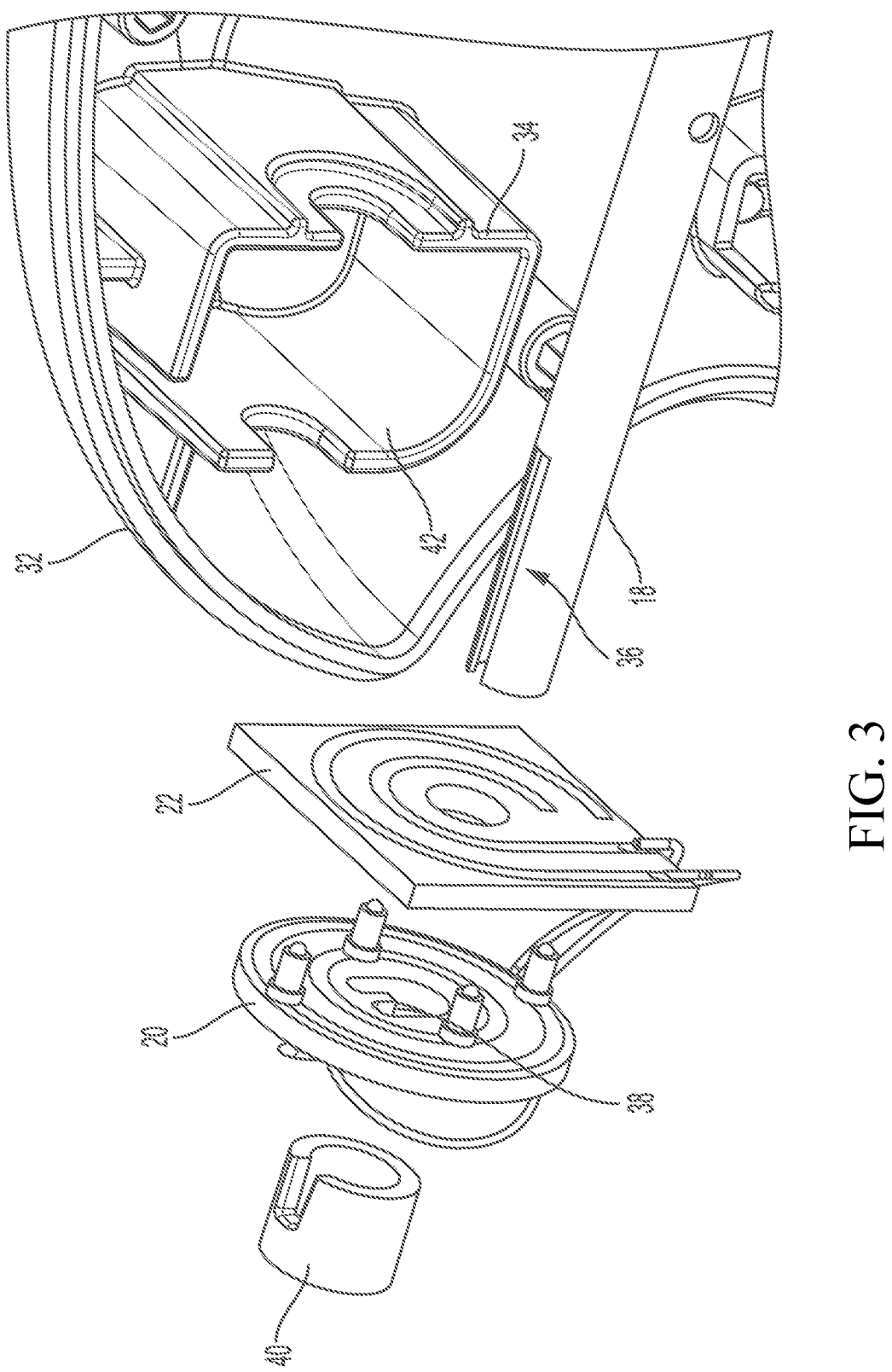
FIG. 3 is an exploded view of an assembly for providing electrical continuity and continuous rotation in a surgical device according to the present invention.

Referring to FIG. 2, continuous rotation assembly 12 comprises a rotor 20 held in continuous contact with a stator 22. Rotor 20 carries first and second sets of conductive pins 24 and 26 that are electrically isolated from each other. Stator 22 supports first and second rings 28 and 30 that are electrically isolated from each other and are aligned to mate with first and second sets of pins 24 and 26, respectively. For example, first and second rings 28 may be positioned concentrically around shaft 18. Stator 22 is fixed within a housing 32 of device 10, such as by a first rib 34 formed within the interior of housing 32. Rotor 20 is coupled to shaft 18 of device 10 that supports jaws 14 for rotation therewith. For example, shaft 18 may include a slot 36 that accepts a tang 38 of rotor 20 and imparts rotational force to rotor 20 if shaft 18 is rotated.

As seen in FIG. 2, first set of pins 24 are positioned to be in contact with first ring 28. Second set of pins 26 are positioned to be in contact second ring 30. First and second sets of pins 24 and 26 are preferably pogo pins that have spring loaded tips to maintain secure electrical contact with first and second rings 28 and 30 during any rotation of rotor 20 relative to stator 22. A bearing 40 may be positioned in abutting relation to a second rib 42 within housing 32 and to rotor 20 to keep rotor 20 in contact with stator 22 so that contact is maintained between first and second pins 24 and 26 corresponding conductive rings 28 and 30.

A first pair of wires 46 and 48 may be coupled to first and second sets of pins 24 and 26, respectively, via contact pads 50. Wires 46 and 48 extend within shaft 18 to connect to electrodes held within jaws 14. First pair of wires 46 and 48 will rotate along with rotor 20 and shaft 18 and thus will not come under any tension regarding of how shaft 18 is rotated. A second set of wires 52 and 54 interconnects each of rings 28 and 30 to electrosurgical power source 16. As a result, electrosurgical power source 16 is electrically interconnected to jaws 14 such as for cutting and coagulation procedures. If shaft 18 of device 10 is rotated about longitudinal axis X-X during an electrosurgical procedure, rotor 20 will rotate along with shaft 18 while stator 22 remains stationary. First and second sets of pins 24 and 26 of rotor 20 will remain in contact with rings 28 and 30, respectively, during any rotation. As stator 22 is fixed in place, wires 52 and 54 are not required to move or stretch along with rotation of shaft 18, and will therefore not become inadvertently disconnected regardless of how shaft 18 is rotated. As a result, electrical continuity between jaws 14 and electrosurgical power source 16 is maintained regardless of the extent of rotation of shaft 18. In fact, shaft 18 may be rotated continuously while still maintaining electrical connectively between jaws 14 and electrosurgical power source 16 without concern of loos of electrical continuity due to disconnected wires or electrical components.

What is claimed is:

1. An electrosurgical device, comprising:
a housing defining a first rib and a second rib;
an electrosurgical implement supported by a shaft for rotation about a longitudinal axis, wherein the shaft includes a longitudinal slot;
a stator positioned about the shaft and fixed against rotation, wherein the stator includes a pair of concentrically positioned rings that are electrically isolated from each other and configured for connection to an electrosurgical power source, wherein the stator is positioned in abutting relation to the first rib such that the first rib prevents rotation of the stator;
a rotor having first and second sets of pins that are electrically isolated from each other and electrically coupled to the electrosurgical implement, wherein the first set of pins are positioned concentrically, and the second set of pins are positioned concentrically, and wherein the rotor is positioned about and rotatable with the shaft such that the first set of pins are positioned in contact with one of the pair of rings and the second set of pins are positioned in contact with the other of the pair of rings, wherein the rotor includes a tang that engages the slot of the shaft; and
a bearing positioned between the rotor and the second rib and in abutting relation to the rotor and the second rib so that the rotor can rotate while contact is maintained between the first set of pins and the one of the pair of rings and between the second set of pins and the other of the pair of rings.

2. The electrosurgical device of claim 1, wherein the electrosurgical implement comprises first and second opposing jaws, wherein each of the first and second opposing jaws is electrically coupled to a respective one of the first and second sets of pins by each of a second pair of wires.

3. A method of providing continuous rotation to an electrosurgical device, comprising the steps of:
providing a housing defining a first rib and a second rib and supporting a shaft of the electrosurgical device for rotation about a longitudinal axis, wherein the shaft includes a slot;
coupling a rotor having first and second sets of pins electrically isolated from each other and positioned concentrically to the shaft of the electrosurgical device so that the first set of pins are positioned in contact with one of a concentrically positioned pair of rings of a stator that is fixed against rotation and the second set of pins are positioned in contact with the other of the pair of rings, wherein the rotor includes a tang that engages the slot of the shaft and the stator is positioned in abutting relation to the first rib such that the first rib prevents rotation of the stator;
providing a bearing between the rotor and the second rib and in abutting relation to the rotor and the second rib so that the rotor can rotate while contact is maintained between the first set of pins and the one of the pair of rings and between the second set of pins and the other of the pair of rings;
coupling the first and second sets of pins to an electrosurgical implement of the electrosurgical device that is mounted to the shaft; and
coupling the pair of rings of the stator to an electrosurgical power source so that the electrosurgical power source is in electrical continuity with the electrosurgical implement.

4. The method of claim 3, further comprising the step of rotating the shaft to cause rotation of the rotor while the stator remains fixed so that electrical continuity is maintained between the electrosurgical power source and the electrosurgical implement as a result of the first and second sets of pins remaining in contact with the pair of rings as the shaft is rotated.

5. The method of claim 4, wherein the first and second sets of pins are spring loaded to remain in contact with the pair of rings.

* * * * *